United States Patent
Dijkstra

(10) Patent No.: US 10,428,040 B2
(45) Date of Patent: Oct. 1, 2019

(54) **PROCESSES FOR THE ISOLATION OF A CANNABINOID EXTRACT AND PRODUCT FROM *CANNABIS* PLANT MATERIAL**

(71) Applicant: Albert Jan Dijkstra, Ghent (BE)

(72) Inventor: Albert Jan Dijkstra, Ghent (BE)

( * ) Notice: Subject to any disclaimer, the term of this patent is extended or adjusted under 35 U.S.C. 154(b) by 0 days.

(21) Appl. No.: 16/125,457

(22) Filed: Sep. 7, 2018

(65) Prior Publication Data
US 2019/0077781 A1 Mar. 14, 2019

(30) Foreign Application Priority Data
Sep. 12, 2017 (EP) ..................... 17306175

(51) Int. Cl.
*C07D 311/80* (2006.01)
*A61K 36/185* (2006.01)
*B01D 11/02* (2006.01)

(52) U.S. Cl.
CPC .......... *C07D 311/80* (2013.01); *A61K 36/185* (2013.01); *B01D 11/0288* (2013.01); *B01D 11/0296* (2013.01); *A61K 2236/00* (2013.01)

(58) Field of Classification Search
CPC .................................................. C07D 311/80
USPC ....................................................... 549/390
See application file for complete search history.

(56) References Cited

U.S. PATENT DOCUMENTS

| | | | |
|---|---|---|---|
| 6,630,507 B1 | 10/2003 | Hampson et al. | 514/454 |
| 7,622,140 B2 | 11/2009 | Whittle et al. | 424/725 |
| 8,445,034 B1 | 5/2013 | Coles, Jr. | 424/725 |
| 8,895,078 B2 | 11/2014 | Mueller | 424/725 |
| 9,649,349 B1 | 5/2017 | Tucker et al. | A61K 36/185 |
| 2012/0046352 A1 | 2/2012 | Hospodor | 514/454 |
| 2015/0126754 A1 | 5/2015 | Fernandez Cid et al. | C07D 311/80 |
| 2015/0152018 A1* | 6/2015 | Raber | C07D 311/80 549/390 |
| 2016/0213720 A1 | 7/2016 | Barringer | A61K 36/185 |
| 2016/0326130 A1 | 11/2016 | Changoer et al. | C07D 311/80 |
| 2017/0008870 A1 | 1/2017 | Dibble et al. | C07D 311/80 |

FOREIGN PATENT DOCUMENTS

| | | | |
|---|---|---|---|
| CA | 2872528 | 11/2013 | A61K 31/35 |
| WO | WO2004026857 | 4/2004 | C07D 311/80 |
| WO | WO2017026897 | 2/2017 | B01D 11/00 |
| WO | WO2017/137992 | 8/2017 | A61K 9/16 |

OTHER PUBLICATIONS

Citti et al., "Medicinal cannabis: Principal cannabinoids concentration and their stability evaluated by a high performance liquid chromatography coupled to diode array and quadrupole time of flight mass spectrometry method," Journal of Pharmaceutical and Biomedical Analysis, Aug. 31, 2016, vol. 128, pp. 201-209 (9 pgs).
European Search Report issued in application EP 17 30 6175, dated Mar. 20, 2016 (3 pgs).
Hazekamp, A., "Cannabis; extracting the medicine," doctoral thesis, University of Leiden, Sep. 5, 2007 (187 pgs).
Morini et al., "Therapeutic Use of Δ9-THC and Cannabidiol: Evaluation of a New Extraction Procedure for the Preparation of *Cannabis*-based Olive Oil," Current Pharmaceutical Biotechnology, Jan. 1, 2017, vol. 18, No. 10, pp. 828-833 (6 pgs).

\* cited by examiner

*Primary Examiner* — Taofiq A Solola
(74) *Attorney, Agent, or Firm* — Hayes Soloway P.C.

(57) ABSTRACT

Disclosed are processes for obtaining a cannabinoid extract and product from *Cannabis* plant material. This way cannabinoids can be isolated in a way that produces higher yields than prior art methods. The disclosed processes to almost pure cannabinoids. In addition the disclosed processes can be carried out easily on a large scale in an economically advantageous manner.

20 Claims, No Drawings

PROCESSES FOR THE ISOLATION OF A CANNABINOID EXTRACT AND PRODUCT FROM CANNABIS PLANT MATERIAL

FIELD OF THE INVENTION

The present invention relates to processes for obtaining a cannabinoid extract and product from Cannabis plant material.

BACKGROUND OF THE INVENTION

With the expanding legalisation of the medical and recreational use of cannabinoids there is an urgent need for a simple and effective process that isolates these cannabinoids from their raw material, marihuana. This process should have a high extraction yield and provide cannabinoid products with a purity that meets pharmaceutical standards.

Several processes have been developed to isolate pure cannabinoids from marihuana. U.S. Pat. No. 8,895,078 discloses a process using supercritical carbon dioxide as the extraction solvent. However, this solvent also extracts waxes, terpenes, glyceride oils, phosphatides and colouring compounds from the marihuana so that the extract requires extensive purification, which purification inevitably leads to loss of cannabinoids.

The extraction process disclosed in WO 2004/026857 uses ethanol or hexane as extraction solvent. Both solvents are inflammable and thus require an X-proof extraction facility which increases the investment required and the extract also requires purification. Such a purification process has been disclosed in CA 2,872,528, which process comprises thin film evaporation of the extract followed by flash chromatography of the distillate. The equipment concerned implies that the process can only be carried out at laboratory scale. That also holds for the centrifugal partition chromatographical method described in the doctoral thesis of Arno Hazekamp (Leiden, 2007).

In a more recent patent application (US 2015/0126754), a high purity $\Delta^9$-tetrahydrocannabinol (THC) isolate is produced from a crude solvent extract by subjecting this extract to thin film evaporation, chromatographically fractionating the refined extract to obtain high purity fractions and subjecting the high purity fractions to another thin film evaporation. Again, the process comprises many steps and is only suitable for small scale preparations. An extraction process using multiple solvents has been disclosed in US Patent Application Publication US 2016/0326130. Marihuana flowers are first of all extracted with a non-polar organic solvent wherein the yield is approximately 50-70% with respect to the main cannabinoids. Then the organic extract is extracted with an aqueous base and subsequently, multiple extractions with tert-butyl methyl ether, washing with water, extraction with pentane, treatment of the pentane miscella with activated carbon are necessary to arrive at a purified $\Delta^9$-tetrahydrocannabinol product. It uses large amounts of solvents and thereby generates large amounts of waste and effluents.

WO 2017/026897 A1 discloses a laboratory extractor for contacting marihuana with the extraction solvent ethanol. US Patent Application Publication US 2017/0008870 discloses a process to extract marihuana with a solvent and cooling the solvent extract so that a precipitate is formed and removing the precipitate by filtration. By further cooling to temperatures as low as −50° C. or even −85° C., a cannabinoid precipitate is formed that is collected. In the example, two 300 mL cans of butane are used to extract only 50 g of Cannabis plant material which may contain only 5 g of cannabinoids, which makes it an expensive process.

Another process for the isolation of cannabinoids from marihuana has been disclosed in U.S. Pat. No. 7,622,140. In this process the cannabinoids are volatilized by contacting the Cannabis plant material with a gas that has been heated to a temperature above 100° C. that is sufficiently high to volatilize at least one cannabinoid but not so high as to cause pyrolysis of the Cannabis plant material, and condensing the vapour and collecting the condensate.

In summary, current processes to isolate cannabinoids from their raw material (marihuana) comprise a large number of steps: harvesting the trichomes from the female plants, comminuting the trichomes, drying the comminuted trichomes, extracting the dried plant material with a solvent like supercritical carbon dioxide, collecting the extract, dissolving the extract in ethanol and cooling it so as to precipitate the waxes, removing the waxes by filtration, treating the alcoholic filtrate with activated carbon to remove colouring compounds, removing this carbon adsorbent by filtration, and finally, evaporating the alcoholic solution to dryness. This leads to a mixture of cannabinoids the composition of which reflects the raw material and if these were to be decarboxylated and/or separated that would entail further processing steps. Besides, each step leads to a yield loss and given the selling price of purified cannabinoids, this constitutes a serious disadvantage. Moreover, current processes operate at laboratory scale which means that there is a need for a simple process that isolates cannabinoids from Cannabis plant material in high yield and that can be executed at a sufficiently large scale to meet market demands.

SUMMARY OF THE INVENTION

The inventor has surprisingly found that the disadvantages of the prior art methods can be overcome by a process for obtaining a cannabinoid extract from Cannabis plant material wherein plant material comprising cannabinoids derived from one or more Cannabis plants is first suspended in an oil before isolation of the cannabinoids from said oil.

In a first aspect, the invention relates to a process for obtaining a cannabinoid extract from Cannabis plant material comprising the steps of:
  a) providing a dispersion of material comprising cannabinoids derived from one or more Cannabis plants in an oil;
  b) isolating at least a portion of said cannabinoids from said dispersion to obtain a cannabinoid extract.

In a second aspect, the invention relates to a process for obtaining a cannabinoid product, comprising the steps of obtaining a cannabinoid extract in accordance with the first aspect of the invention; and adding one or more flavours or aromas to said extract.

DETAILED DESCRIPTION OF THE INVENTION

The present invention is based on the finding that when in a process for obtaining a cannabinoid extract from Cannabis plant material, Cannabis plant derived material is first dispersed in an oil before isolation of the cannabinoids contained therein, these cannabinoids can be isolated in a way that produces higher yields than prior art methods. The process of the invention leads to almost pure cannabinoids. In addition the process of the invention can be carried out easily on a large scale in an economically advantageous manner.

In the process according to the invention *Cannabis* plant derived material is used as raw material for the isolation of cannabinoids. This *Cannabis* plant derived material may encompass whole plants but preferably parts thereof that contain the principal medically or recreationally active ingredients, for example the aerial parts of the plant or isolated leaves, stems or flowering heads with the trichomes containing most of the cannabinoids. According to the process of the invention, *Cannabis* plant material may be freshly harvested plant material or dried material. In fact, for the process according to the invention, the water content of the raw material is immaterial since this water will be removed during said process anyway.

It is also possible that the cannabis plant material has already been subjected to a partial extraction before being treated in the process of the invention. The term "*Cannabis* plant derived material" may also relate to plant parts as well as mixtures of compounds derived from *Cannabis* plants that still need further purification of the cannabinoids contained therein.

In this light it is to be understood that the term "dispersion" as referred to in the present invention may be a solution or a suspension. Throughout this application the terms "suspension" and "slurry" have the same meaning and are used interchangeably. Therefore the dispersion may be in the form of a solution containing cannabinoids and other compounds. Such a solution may be prepared from a marihuana extract that has been purchased externally and has been produced by extracting *Cannabis* plant material, for instance with a non-polar solvent such as butane or carbon dioxide, and that requires purification according to the process of the invention because it contains one or more non-cannabinoid impurities like waxes and colouring compounds.

In another embodiment the dispersion is in the form of a suspension containing *Cannabis* plant pieces. Such plant pieces are suitably larger than 0.1 mm in at least one of their dimension and encompass plants or plant parts, for instance ground plant material or plant material that is chopped into pieces. In the latter case, the chopped material may then be fed into a slurry vessel to form a suspension. Depending on the scale of operations, this slurry vessel may be the same vessel as the one used during extraction. The vessel may be provided with a mechanical disperser, the purpose of which is to finely divide the plant material so that the access of the solvent to the cannabinoids and their rate of dissolution are improved.

The access of the oil can also be improved by applying ultrasonics or a pulsed electric field to the slurry vessel during at least part of the dispersing stage.

In the context of the invention, the term "cannabinoids" is meant to refer to compounds derived from *Cannabis* plants that act on cannabinoid receptors in cells that alter neurotransmitter release in the brain. These cannabinoids are concentrated in the trichomes of the plants. Non-limiting examples of cannabinoids in the context of the invention include tetrahydrocannabinol, cannabidiol, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, cannabicitran and their carboxylic acids. Accordingly, in the method of the invention at least one of the cannabinoids selected from this group is isolated from the oily dispersion in step b). It is highly preferred that the cannabinoid extract contains at least tetrahydrocannabinol, in particular $\Delta^9$-tetrahydrocannabinol. Accordingly, preferably fractions containing at least $\Delta^9$-tetrahydrocannabinol are taken to prepare the cannabinoid extract. Such fractions preferably contain $\Delta^9$-tetrahydrocannabinol in high purity.

In principle any oil or oil mixture qualifies for dispersing material comprising cannabinoids derived from one or more *Cannabis* plants in it in accordance with the invention. With "oil" is meant any nonpolar chemical substance that is a viscous liquid at ambient temperatures and is both hydrophobic and lipophilic. A preferred oil for purposes of this invention is a vegetable oil.

Suitable examples of such vegetable oils are soybean oil, rapeseed oil, corn germ oil or sunflower seed oil, but more exotic oils such as hemp seed oil can also be used in the process according to the invention. In principle it would even be technically possible to use cannabis oil itself for purposes of dispersing material comprising cannabinoids derived from one or more *Cannabis* plants in it, but for commercial reasons it is preferred not to use cannabis oil. For stability reasons, the oil to be used has preferably a low polyunsaturated fatty acid content and for ease of handling, it preferably has a low saturated fatty acid content. Accordingly, a high oleic sunflower seed oil is considered to be highly suitable for the process according to the invention.

On the other hand, also mineral oils can suitably be used. An example is medicinal liquid paraffin, also known as paraffinum liquidum.

Whereas vegetable oils contain one or more antioxidants, the liquid paraffin does not. Therefore, in such a case it is preferred that one or more antioxidants are added to the oil to protect the cannabinoids against oxidation. These antioxidants should not be volatilized during the subsequent vacuum stripping process so butylated hydroxytoluene (BHT) is less suitable because of its volatility. Propyl gallates are less volatile and are therefore preferred. On the other hand, some volatile antioxidant may be added in conjunction with a non-volatile antioxidant to protect the condensate against oxidation.

It is preferred to add the plant material gradually to the oil. This way, properties of the suspension such as solids content and viscosity can be accurately controlled. For an efficient execution of the process according to the invention, the suspension strength and its cannabinoid content are preferably as high as possible given the handling constraints of the processing equipment. For this reason, it may be advantageous to heat the suspension while it is being prepared for instance by using a jacketed vessel or internal heating coils. The oil to be introduced into a slurry vessel may vary in temperature and for this reason, the possibility to control the temperature of the vessel contents allows a constant final suspension temperature to be attained.

It is preferred that isolation of the cannabinoids from the oily dispersion comprises one or both of A) stripping said dispersion under reduced pressure with a gaseous stripping medium to extract at least a portion of said cannabinoids from said dispersion into said gaseous stripping medium to obtain a vapour containing cannabinoids; condensing at least part of said vapour to form a condensate; and recovering a cannabinoid extract from said condensate;

B) mixing said dispersion with a polar solvent, and forming a two-phase system with a first phase of said dispersion and a second phase of said polar solvent, wherein at least part of the cannabinoids is extracted into the second phase; isolating at least part of the second phase from the first phase; and wherein the extraction is optionally followed by evaporating at least part of said isolated second phase to obtain a cannabinoid containing evaporation residue. This will be further explained hereafter.

The inventor has found that the isolation of cannabinoids from the oily suspension can be suitably carried out by the use of a gaseous stripping medium or by the use of a polar solvent. Therefore, in one embodiment in the process according to the invention the isolation comprises treatment of said dispersion with a gaseous stripping medium or a polar solvent, to isolate at least a portion of said cannabinoids from said dispersion into said gaseous stripping medium or said polar solvent.

During isolation, suitable fractions are extracted and collected. The inventor has observed that various fractions may be obtained, among which fractions containing terpenes, fractions containing compounds that adversely influence taste, smell and/or appearance or other compounds that are of no use in a cannabinoid product, and fractions that contain cannabinoids. From the latter fractions, suitable fractions are isolated and optionally concentrated to provide a cannabinoid extract. Suitable fractions contain high purity of one or more cannabinoids.

In one preferred embodiment, a vacuum stripping process is used to extract the cannabinoids from the oil to isolate the cannabinoids. It has been found that this embodiment is in particular suitable for isolating cannabinoids from crude cannabinoid plant material such as a dispersion in the form of a suspension containing parts of plants, such as chopped pieces of plants. In this embodiment step b) comprises: stripping the dispersion under reduced pressure with a gaseous stripping medium to extract said cannabinoids from said dispersion into said gaseous stripping medium to obtain a vapour containing cannabinoids; condensing at least part of said vapour to form a condensate; and recovering said cannabinoid extract from said condensate.

The oil is preferably stripped under vacuum before being used in the process according to the invention to prevent malodorous compounds present in the oil being removed and condensed at the same time as the cannabinoids.

The vacuum stripping treatment will not only remove the cannabinoids from the dispersion but all compounds that are volatile under the stripping conditions in force. Accordingly, any water present in the dispersion will be removed, which is why the water content of the *Cannabis* plant material used in the process according to the invention is of no significance, and the *Cannabis* plant material need not be dried.

In addition to this water, other volatiles like terpenes, malodourous compounds and thermal decomposition products of the plant material will be stripped out of the dispersion. At what temperature most of these compounds will be removed depends on their volatility, which volatility depends inter alia on the temperature of the dispersion. It is preferred that the process of the invention is carried out as a batch process, because when the process according to the invention is carried out as a batch process, a successive removal of volatiles can be realized by a gradual heating of the dispersion. It is also possible to maintain a relatively high concentration of cannabinoids in the oil by interrupting the batch stripping process before the dispersion is depleted and dispersing a further amount of cannabinoid containing plant material or a fresh amount of a dispersion comprising cannabinoid containing plant material in the partially depleted dispersion and continuing vacuum stripping.

The vapour pressures of the individual cannabinoids differ, so during vacuum stripping there will be some preferential evaporation. Consequently, the composition of the condensate will not be identical to the cannabinoid composition of the crude plant material. Moreover, the cannabinoid composition of the condensate may vary in time. Early condensates will be enriched in the most volatile cannabinoids but when their concentration in the oil decreases, so does their rate of volatilization and thus their concentration in the condensate.

Various stripping media can be used in the process of the invention but water vapour is preferred. Water has a relative molecular mass of 18 so the amount to be used to attain a certain result is relatively small; besides, it is cheap and inert. Nitrogen (relative molecular mass equals 28) can also be used but it has the disadvantage that it does not condense so that the vacuum pump system has to compress the entire stripping medium introduced into the stripping vessel to atmospheric. Methanol has a relative molecular mass of 32 and has the advantage that at low temperatures, it will condense without solidifying. Accordingly, methanol can be advantageously used in continuous operations since it permits continuous removal of condensate from low-temperature condensing systems in which water would freeze; moreover, cannabinoids are fairly soluble in methanol.

The stripping medium can be introduced into the stripping vessel in a number of ways. In large continuous installations one suitable way is to use mammoth pumps. They ensure a good contact between the stripping medium and the oil and are the preferred equipment for large installations. Smaller installations can use a hollow ring with holes along its circumference below the surface of the liquid.

During the vacuum stripping step the oil is preferably heated. It is preferred to maintain the temperature of said oil below 250° C., more preferably up to a maximum of 240° C. in order to prevent release of bad odours. This affects the amount of stripping medium required to remove the cannabinoids from the dispersion and thus the period of time during which the dispersion is stripped at its final temperature. This period of time also affects the decarboxylation of the cannabinoic acids, which is important to render the cannabinoids in their psychomimetically active form. Decarboxylation of for instance $\Delta^9$-tetrahydrocannabinolic acid results in the psychomimetically active form $\Delta^9$-tetrahydrocannabinol. In general, the periods of time and the temperatures used in the process according to the invention will suffice to ensure a sufficient degree of decarboxylation of cannabinoic acids present in the dispersion but if this turns out to require a further heat treatment, this can be provided by extending the period of time the dispersion is held at the final stripping temperature.

For example, in a suitable embodiment of the process of the invention the dispersion is vacuum stripped by sparging vapour, such as water vapour, while its temperature is gradually increased. The dispersion may in a first step be heated to 100° C. at which a light fraction of terpenes including pinene, limonene, myrcene and linolool are stripped from the oil. Upon further increase of the temperature to 150° C. a further fraction comprising the heavier sesquiterpenes such as caryophyllene, humulene and valencene are stripped from the oil. Furthermore, at these temperatures the cannabinoic acids decarboxylate and carbon dioxide is liberated. The temperature can then be further raised to about 200° C. to extract further material. In general this material has an unpleasant taste and this fraction in general will be discarded. By further increasing the temperature stepwise to a temperature of 240° C., cannabinoids can then be extracted from the oily dispersion. The presence of terpenes influences the aroma and flavour of cannabis products. The cannabinoid fraction(s) may be recombined with one or more of the terpene fractions depending on the desired aroma and flavour profile of the cannabinoid product. Alternatively, one may use the pure cannabinoid extract or add suitable flavours or aromas to it.

How to heat the batch of oil and cannabinoid containing material to be extracted is known to those skilled in the art and depends very much on the scale of operation of the process according to the invention. On a laboratory scale, an electric heating mantle will usually suffice. The output of this mantle can be controlled by measuring the temperature of the dispersion. On pilot plant scale, providing the stripping vessel with a jacket that can be heated by a thermal heating fluid may be easier to control and when the surface to volume ratio has to be increased, heating coils inside the stripping vessel will provide the answer to this problem. In order to get a proper heat transfer between the dispersion and the heat exchange surfaces, agitation is necessary. This agitation is provided by the stripping medium that expands under vacuum and causes the liquid to boil. This is one of the reasons why stripping conditions (vacuum and flow rate of stripping medium) may be established before heating is started but starting to heat earlier also falls within the scope of the process according to the invention.

For practical reasons and for the sake of efficiency of the vacuum stripping it is preferred that during the vacuum stripping step the pressure is maintained below 20 mbar absolute, preferably below 10 mbar absolute, and more preferably below 5 mbar absolute. Maintaining the vacuum in the stripping vessel requires one or more vacuum pumps. In principle, steam ejector batteries with interspersed condensers can be used for this purpose, whereby these volatiles are condensed by the cooling water condensing the motive steam, or they can be condensed in a separate scrubber. However, these condensation processes are more focused on removal of volatiles than on isolating these volatiles in as pure a state as possible. Consequently, the process according to the invention preferably employs mechanical vacuum pumps in combination with surface condensers.

It is preferred that the vapour containing said cannabinoids that is obtained during the stripping step is compressed before being at least partially condensed. Accordingly, the pump nearest to the stripping vessel can be a Roots blower that compresses the vapour leaving the vessel to some 50 mbar and thus maintains a pressure of 3-5 mbar absolute in said stripping vessel. When this vapour is passed along a surface condenser that is cooled by liquid ammonia, all volatiles including the water if used as stripping medium will condense and solidify so that a relatively small pump can be used to maintain the vacuum in the condensing section; a small water ring pump can be used for this purpose. However, the process according to the invention is not limited to these types of pumps that have only been mentioned by way of illustration.

Instead of using a surface condenser that is cooled by liquid ammonia, it is also possible to maintain a higher temperature in said condenser. Then, the temperature can be made too high for the steam to condense but low enough to condense the cannabinoids. This embodiment of the process according to the invention has the advantage that it obviates the separation of the cannabinoids from the water used as stripping medium. The water passing through the condensation system will condense in the water ring pump if such a pump is used.

It is preferred that the dispersion of oil and cannabinoid containing material to be extracted is heated gradually while vacuum and stripping conditions have already been established. This means that the volatiles that are removed by the process according to the invention will also emerge gradually, which allows some kind of fractionation. A preferred embodiment of the process according to the invention therefore comprises two or more low temperature surface condensers in series that permit successive isolation of the various fractions. If these fractions are solid at the condenser temperature, it may be advantageous to install two condensers in parallel and switch from one condenser to the other while thawing, emptying and preparing the original one.

If steam is used as stripping medium, freezing it onto the surface of the condensers has the advantage that the load on the final vacuum pump is reduced to the air that leaks into the system. In fact, the condenser itself then acts as a powerful vacuum pump and permits the capacity of the other pumps to be reduced.

Maintaining the temperature of the surface condensers at a temperature at which the water used in the vacuum stripping treatment will freeze requires a coolant like liquid ammonia or a glycol/water mixture. Refrigeration plants that will ensure the low temperature are well-known and commonly available.

Gradual heating and surface condensation onto interchangeable surface condensers will permit a first condensate to be isolated that will have a high terpene concentration and a final condensate that provides almost pure cannabinoids according to the process of the invention.

In the embodiment of the process according to the invention in which the vapours leaving the stripping vessel are frozen onto the surface of a condenser, the final condensate consists primarily of water used as stripping medium and cannabinoids. The latter do not dissolve in water so that melting and warming said condensate leads to a two phase system. The lower phase consists of dirty water that is to be discarded and the upper phase consists of almost pure cannabinoids that can be isolated by sheer phase separation.

The stripping process may also be carried out continuously. In this case, all volatile compounds are removed simultaneously but they can be collected separately by using two or more condensers in series whereby the first condenser that is reached by the vapour stream operates at a surface temperature at which the least volatile components of the vapour stream will condense selectively and the last condenser has a surface temperature that will cause the most volatile of the condensable components to condense or even freeze.

Although some chemical reactions may occur during the vacuum stripping process like the thermal decomposition of colouring compounds such as carotenes and the decarboxylation of cannabinoic acids, the vacuum stripping process is basically a physical process. It can be described by the simplified Bailey equation:

$$S = \frac{PO}{EP_v} \ln \frac{V_s}{V_e}$$

in which:
S=amount of stripping medium (mol)
P=system pressure (pressure units)
O=amount of oil being processed (mol)
E=evaporation efficiency (no dimensions)
$P_v$=pressure of pure volatile compound (pressure units)
$V_s$=amount of volatiles before stripping (mol)
$V_e$=amount of volatiles after stripping (mol As is only to be expected, the amount of stripping medium that is required to achieve a certain extent of volatile removal is proportional to the amount of oil being processed. It is also proportional to the system pressure but since the volume occupied by the stripping medium is inversely proportional to the system pressure, it follows that the extent of the volatile removal is really determined by the volume of the stripping medium. Because of the low system pressure, this volume is very large in comparison with the amount of oil being treated.

The amount of stripping medium is inversely proportional to the vapour pressure of the volatile compound. Since this vapour pressure increases with temperature, this means that less stripping medium is required to achieve the same extent of volatile removal when the temperature of the oil being stripped is increased. The stripping medium requirement also depends on the equipment being used. If this ensures a good contact between stripping medium and the oil being stripped and if reflux of condensed vapours into the oil is prevented, the evaporation efficiency will be close to unity.

Finally, the stripping medium requirement is proportional to the logarithm of the ratio of the volatiles content before and after the stripping treatment. So if a certain amount of stripping medium suffices to half the volatile content, using the same amount again will also half the residual volatiles so that a quarter of the original amount is left. This means that whatever the amount of stripping medium used, there will always be some volatile compound left in the oil.

In this respect, the vacuum stripping process differs fundamentally from a steam distillation process. In the latter process, the volatile compound is not dissolved but forms a separate phase and its rate of evaporation does not decrease until said separate phase has been evaporated.

The vacuum stripping process may be continued until the residual cannabinoid content of the dispersion has been reduced to such an extent that recuperating part of this residual content is more costly than the value of the recuperated cannabinoids. Nevertheless, sometimes the extraction process is not complete and a substantial amount of cannabinoids remains in the oil after vacuum stripping. A further treatment that extracts the remaining cannabinoids can then be carried out using a solvent extraction step using a polar solvent. Because extraction according to this embodiment is carried out at a lower temperature than the vacuum stripping extraction, this embodiment reduces the period of time that the *Cannabis* plant material has to be exposed to high temperatures and may thus affect the extent of decarboxylation of the cannabinoic acids.

In this embodiment the isolation of cannabinoids comprises mixing said dispersion with said polar solvent, and forming a two-phase system with a first phase of the oily dispersion and a second phase of said polar solvent, wherein at least part of the cannabinoids is extracted into the second phase. Subsequently, at least part of the second phase is isolated from the first phase and from this isolated second phase the extract is prepared. This extraction can be carried out for instance if the cannabinoid concentration in the oil is still too high after the abovementioned extraction by means of vacuum stripping, but it is well possible to perform this extraction on any other dispersion described in this application, such as a suspension containing parts of plants, such as chopped pieces of plants. The extraction is optionally followed by evaporating at least part of said polar solvent to obtain a cannabinoid containing evaporation residue. This evaporation residue can be subjected to further steps of extracting and isolating the cannabinoids contained therein.

The polar solvent is a liquid solvent and is not or poorly miscible with the oil, i.e. upon mixing of the oil and the polar solvent no homogeneous mixture is formed. Ethanol is an example of a solvent meeting these requirements since at ambient temperatures, the solubility of oil in ethanol is negligible, especially when the ethanol contains some water. Aqueous isopropanol is another example of a suitable extraction solvent especially since its dissolving power can be controlled via its water content. However, care should be taken to maintain a specific density difference between the oil and the aqueous isopropanol.

Suitable solvents may be selected from the group consisting of methanol, ethanol, isopropanol, water and mixtures thereof. Ethanol can be suitably used as the polar solvent.

When choosing the extraction solvent (i.e. said polar solvent as referred to in this application), care must be taken to avoid accumulation of unwanted plant constituents, and other compounds that dissolve in the solvent and that are not removed by vacuum stripping or thermal decomposition. If these compounds were to dissolve in the extraction solvent, they would be re-introduced in a slurry vessel via the evaporation residue and accumulate. Therefore, it may be preferred to alternate between different solvents in the course of time. In that case, the solvent that is used after an earlier used solvent may function as a purge for removing these unwanted plant constituents.

This liquid/liquid solvent extraction can be carried out in several ways known to those skilled in the art. The use of a Kühni agitated extraction column has been shown to be an effective manner to remove the cannabinoids from the dispersion. Mixer-settler equipment can also be used for this purpose.

Although it is possible in the process according to the invention to carry out the isolation of cannabinoids without said vacuum stripping step, it is preferred that the extraction comprises a combination of said vacuum stripping step and said solvent extraction step because solvent extraction often leads to coloured products.

Therefore, in a further embodiment of the process according to the invention, the isolation comprises stripping the oily dispersion under reduced pressure with a gaseous stripping medium to obtain a vapour containing cannabinoids and a dispersion with reduced cannabinoids content, and performing a further extraction on said dispersion with reduced cannabinoids content, which comprises treatment with a polar solvent thereby forming a two-phase system with a first phase of said dispersion and a second phase of said polar solvent, wherein at least part of the cannabinoids from the dispersion with reduced cannabinoids content is extracted into the second phase, isolating at least part of the second phase from the first phase and optionally evaporating at least part of said isolated second phase to obtain a cannabinoid containing evaporation residue. Optionally said cannabinoid containing evaporation residue is dissolved in oil to form a miscella. This miscella can be added to the dispersion of the abovementioned step a) for further extraction in accordance with any of the embodiments described above.

After performing an initial extraction such as said solvent extraction and/or said vacuum stripping extraction, the remaining cannabinoids in the dispersion may be further extracted. In particular following a vacuum stripping extraction, the process may comprise the further steps of:

c. separating said dispersion by filtration into a filter cake and a filtrate;

d. performing extraction on said filter cake, which extraction comprises treating the filter cake with a polar solvent, wherein at least part of the cannabinoids is extracted into the polar solvent, and isolating at least a part of said polar solvent containing the extracted cannabinoids;

e. evaporating at least part of said isolated polar solvent from said extract to obtain a cannabinoid containing evaporation residue;

f. dissolving said cannabinoid containing evaporation residue in said filtrate to form a miscella;

g. recycling said miscella into a dispersion which can be subjected again to extraction, for instance as specified above. Suitable polar solvents for this purpose are specified above.

In this embodiment the vacuum stripping process can be interrupted when the cannabinoid content of the oil is still worth recuperating. A reason for this interruption might be the development of undesirable off-flavours by the *Cannabis* plant material because of its exposure to high temperatures for a prolonged period of time. Then the stripped oil still contains residual cannabinoids and is therefore preferably re-used in order that these residual cannabinoids remain in the system. However, this stripped oil may be present in a suspension that still contains extracted plant material that is preferably removed from this oil by separating the suspension into a liquid and a solids fraction. This separation can be effected by filtration or centrifugation. The resulting filtrate or supernatant is preferably used to prepare a new suspension batch so that the cannabinoids present in said liquid fraction can be extracted by vacuum stripping; the filter cake can eventually be discarded. However, this cake retains some oil and the cannabinoids present in this oil would be lost when the cake is discarded. Accordingly, it may be advantageous to extract the filter cake to recover the cannabinoids.

The extraction of the filter cake of step d) can be carried out in several manners. It can be performed in situ by feeding the filtration equipment with the solvent and thereby rinsing the cake. It can also be performed by isolating the filter cake by opening the filter press and suspending this cake in the extraction solvent. The suspension is then sent to another filter which can be a filter press or be of a pressure leaf type. The solvent that now contains cannabinoids from the filter cake is then isolated from the cake. After step d), the isolated filter cake extract is at least partially evaporated and the evaporation residue can be added to the slurry vessel or vacuum stripping vessel where it will dissolve in the oil and from where it will be removed by vacuum stripping. Incomplete evaporation of said solvent does not affect the process according to the invention since any residual solvent will be removed during the subsequent vacuum stripping process; it only affects the economics of the process. After its evaporation, the solvent may be recuperated as condensate; it can be used to extract a subsequent batch of filter cake.

There is, however, another aspect to be considered. The oil that is retained in the filter cake may act as a purge. During the extraction, the cannabinoids are not the only compounds that are extracted. In fact, all lipophilic compounds will be extracted. Accordingly, waxes, phosphatides and acyl glycerides move into the oil and since they are not removed during the vacuum stripping process, they will accumulate in this oil. Accordingly, a purge is needed to prevent these lipophilic compounds from accumulating. The oil that is retained in the filter cake can act as such a purge. It ensures that a dynamic equilibrium will be reached in which the amount of non-volatile lipophilic compounds that leaves the system with the filter cake equals the amount that is introduced by the extraction of the next batch of plant material. In this respect it is preferred that between the abovementioned steps c) and d) steps are carried out of:

c1) rinsing said filter cake with an amount of rinsing oil; and c2) recycling the rinsing oil to a dispersion which can be subjected again to extraction, for instance as specified above.

In the above rinsing step, the amount of rinsing oil is preferably about equal to the amount of oil that is retained by the cake.

In addition to the extracted cannabinoids, the extraction of the filter cake with a solvent like ethanol also yields a solvent-wet filter cake residue. If this residue is positioned on the leaves of a pressure leaf filter, it is possible to remove the solvent by blowing the filter with live steam. The gases leaving the filter can be condensed and the solvent can be recovered by distillation. This system has the advantage that blowing the residue with steam eliminates a fire hazard. On the other hand, the use of a pressure leaf filter may necessitate the use of a filter aid. If a filter press has been used and the cake has been rinsed with the extraction solvent, the cake will contain the possibly inflammable solvent. This cake may then be disposed of.

The extraction process may be continued until recuperating residual cannabinoids from the oily dispersion or filter cake is more costly than the residual cannabinoids are worth. Then the depleted oily dispersion or filter cake that may contain waxes and other non-cannabinoid impurities that were present in the extract can be dumped in its entirety. Alternatively the oil can be recycled to be used again in step a) of the process of the first aspect of the invention.

Another aspect of the invention relates to a process for obtaining a cannabinoid product, comprising the steps of obtaining a cannabinoid extract according to the first aspect of the invention; and adding one or more flavours or aromas to said extract. The cannabinoid product has superior characteristics compared to existing cannabinoid products. Suitable products may be in the form of food grade products such as cooking oil or dairy butter or pharmaceutical product or inhalation products. Depending on the desired product, any suitable carrier or agent may be added to provide the desired characteristics.

Because all compounds that may adversely influence the taste and smell of the cannabinoid product are removed when making the extract, the extract may serve suitably as a base product which can suitably be adapted in composition, e.g. by the addition of flavours or aromas, to meet the wishes of users.

For instance a particular terpene profile comprising one or more terpenes may be added to provide a product with a natural and appealing flavour or odour. Terpenes are organic compounds that affect the aroma and flavour profile of cannabis products. Non-limiting examples of terpenes that are present in *Cannabis* plants include limonene, which confers a citrus flavour/aroma; myrcene, which confers an earthy and musky flavour/aroma; linalool, which confers a floral flavour/aroma with a hint of spice; pinene which confers a pine flavour/aroma; caryophyllene which confers a hoppy flavour/aroma; humulene which confers a sweet flavour/aroma and valencene which confers a citrus flavour/aroma. In that respect it is preferred for the sake of efficiency that the added terpenes are obtained as by-product by means of the above described method for obtaining a cannabinoid extract. Therefore it is preferred that the process for obtaining a cannabinoid product as described herein comprises extracting and separating one or more terpenes from the oily dispersion as defined in respect of the first aspect of the invention, and adding at least a portion of said one or more terpenes to the cannabinoid extract.

EXAMPLES

Example 1

An amount of 2.5 L corn germ oil was introduced into a 5 L three-necked round-bottom flask. The corn oil was purchased at a local supermarket. It had a bland taste and therefore did not need a preliminary vacuum stripping treatment. The three-necked flask was fitted with a thermocouple, a steam inlet and a connection to vacuum and the bottom half was surrounded by an electric mantle. The top half of the flask was covered with fibreglass, insulating the flask to a temperature within 5-10° C. of that of the mixture within the flask. An amount of 1 kg fresh *Cannabis* flowers and trichome covered leaves that tested better than 5-10% cannabinoids by weight were introduced into the flask and mixed with the oil.

After the introduction of the *Cannabis* plant material, the flask was connected to the vacuum system which comprised a splash bulb, a primary surface condenser that was kept at 5° C. by a thermostat and that was fitted with a rotating multi-flask receiver, a dry ice trap kept at −50° C., a mechanical vacuum pump and a vacuum gauge. After the pressure had been reduced to 1 mbar, the contents of the flask were heated to 100° C. To provide agitation sparging water was heated to 100° C. and introduced below the surface of the oil at a rate of approximately 100 mL/h for a period of approximately 30 minutes. This caused mostly terpenes like pinene, limonene, myrcene and linalool to be stripped out of the oil. They were condensed and collected into the receiving flask underneath the primary condenser.

The temperature of the suspension was raised to 150° C., which caused the cannabinoic acids to decarboxylate and liberate carbon dioxide. By introducing further sparging water at a rate of 100 mL/h for 30 minutes a further fraction comprising heavier sesquiterpenes like caryophyllene, humulene and valencene was collected into the same receiving flask under the primary condenser. The combined condensate will be referred to as the 'light fraction'. By raising the temperature to just below 200° C. further material was stripped out of the suspension and collected in a separate flask. This fraction has an unpleasant taste and had therefore to be kept separate so that it could be discarded. Both light fractions were isolated from the system by closing a valve an removed before proceeding.

By raising the temperature to 200-210° C. and continuing stripping by the introducing water at a rate of 100 mL/h cannabinoids started to be extracted from the suspension and continued to do so when the temperature was raised stepwise to 220° C., 230° C. and finally 240° C. at 30 minute intervals. The surface condenser was kept in the range of 60-80° C. so the viscous condensate could easily drip into the receiving flask. Most of the stripping steam passed into the cold trap where it froze. After the suspension had been stripped for 30 minutes at the final temperature, the heating was switched off and when the suspension had cooled down, vacuum was broken and samples were taken for analysis.

The cannabinoid content of this oil sample was determined by isocratic HPLC using a silica column and methanol as solvent. Analysis showed the residual cannabinoid content of the oil to equal 0.63 w %. This means that the oil still contained some 14 g of cannabinoids, which is a low figure in comparison with the 50-100 g that was introduced into the oil, and which implies isolation yields from fresh *Cannabis* flowers and trichome covered leaves of up to 86% and more. This figure could have been lowered by continuing the experiment but since the oil had hardly degraded during the steam stripping process, it could also have been used for a subsequent batch after solids removal. That way, the cannabinoids present in the oil would have been subjected to a subsequent steam stripping process and because their concentration had been increased by the dissolution of the next batch of *Cannabis* plant material, their volatility and rate of vaporisation would also have been increased.

The experiment also illustrates that the process according to the invention allows the cannabinoids to be decarboxylated during their isolation. Analysis of the cannabinoid distillate fraction showed it to contain only 0.92% Δ-9 tetrahydrocannabinol acid as opposed to 38.41% Δ-9 tetrahydrocannabinol, thus demonstrating extensive decarboxylation.

The example also illustrates that the process according to the invention allows of successive collection of volatiles. It enables separate collection of a light fraction comprising terpenes and sesquiterpenes, an undesirable fraction, which the process according to the invention permits to be collected separately and to be discarded and finally the cannabinoid fraction.

Example 2

In this example, a *Cannabis* plant extract containing 54 wt % cannabinoids was purchased on the open market. An aliquot was dissolved in vegetable oil and introduced into a 500 mL flask that was provided with a steam supply. The oil was heated to 250° C. and stripped with steam at a pressure of <1 mbar for 2 hours. The steam was supplied as water heated to 100° C. at a rate of 4 w % of the oil per hour.

Analysis of the distillate showed it to contain 78 w % cannabinoids and the oil contained only 0.50 w % cannabinoids after having been stripped. This example thereby illustrates that the process according to the invention can concentrate cannabinoid extracts by separating the cannabinoids from less volatile compounds. Given the low residual cannabinoid content of the oil, this example also illustrates the high isolation yield of the process according to the invention.

Example 3

An amount of 10 g of purified cannabinoid extract with a cannabinoid content of 84 w % was dissolved in 250 g of vegetable oil. The amount of cannabinoid in the oil was therefore 8.4 gram. An amount of 250 g ethanol was added to this solution and the mixture was shaken several times. The experiment was carried out at room temperature. On standing, it separated into two phases but there was no clear separation between the two phases. Collecting the alcoholic layer and the interphase and removing the alcohol by evaporation left a residue of 15 g with a cannabinoid content of 54%, i.e. 8.1 gram. This means that cannabinoids were isolated from the oil with an efficiency of 96%. Apparently, the ethanol has extracted the cannabinoids from the oil in a seemingly quantitative manner. This means that the process according to the invention allows cannabinoids to be isolated in a really simple manner with high extraction yields. By suspending the *Cannabis* plant material in oil, cannabinoids will be extracted but other oil-soluble compounds such as waxes and triglyceride oils will also be extracted by this oil. These oil-soluble compounds are not soluble in alcohol and can thus be separated from the cannabinoids by alcohol extraction.

The invention claimed is:

1. A process for obtaining a cannabinoid extract from *Cannabis* plant material comprising:
   a) the step of providing a dispersion of material comprising cannabinoids derived from one or more *Cannabis* plants in an oil;
   b) the step of isolating at least a portion of said cannabinoids from said dispersion to obtain a cannabinoid extract, wherein said step of isolating comprises one or both of:
   A) stripping said dispersion under reduced pressure with a gaseous stripping medium to extract at least a portion of said cannabinoids from said dispersion into said gaseous stripping medium to obtain a vapour containing cannabinoids;
   condensing at least part of said vapour to form a condensate; and
   recovering a cannabinoid extract from said condensate; and/or
   B) mixing said dispersion with a polar solvent, and forming a two-phase system with a first phase of said dispersion and a second phase of said polar solvent, wherein at least part of the cannabinoids is extracted into the second phase: isolating at least part of the second phase from the first phase; and wherein the extraction is optionally followed by
   evaporating at least part of said isolated second phase to obtain a cannabinoid containing evaporation residue.

2. The process according to claim 1, wherein said step of isolating comprises:
   A) stripping said dispersion under reduced pressure with a gaseous stripping medium to extract at least a portion of said cannabinoids from said dispersion into said gaseous stripping medium to obtain a vapour containing cannabinoids;
   condensing at least part of said vapour to form a condensate; and
   recovering a cannabinoid extract from said condensate.

3. The process according to claim 1, wherein said step of isolating in step b) comprises:
   b1) stripping said dispersion under reduced pressure with a gaseous stripping medium to extract at least a portion of said cannabinoids from said dispersion into said gaseous stripping medium to obtain a vapour containing cannabinoids;
   b2) condensing at least part of said vapour to form a condensate; and
   b3) recovering a cannabinoid extract from said condensate.

4. The process according to claim 3, wherein, following obtaining said extract in step b), the process comprises the further steps of:
   c. separating said dispersion by filtration to form a filter cake and a filtrate;
   d. performing extraction on said filter cake, which extraction comprises treating the filter cake with a polar solvent, wherein at least part of the cannabinoids is extracted into the polar solvent, and isolating at least a part of said polar solvent containing the extracted cannabinoids;
   e. evaporating at least part of said isolated polar solvent to obtain a cannabinoid containing evaporation residue;
   f. dissolving said cannabinoid containing evaporation residue in said filtrate to form a miscella;
   g. recycling said miscella into the dispersion of step a).

5. The process according to claim 4, which comprises between step c) and d) the steps of c1) rinsing said filter cake with an amount of rinsing oil; and
   c2) recycling the rinsing oil to step a).

6. The process according to claim 1, wherein said step of isolating in step b1 comprises
   stripping said dispersion under reduced pressure with a gaseous stripping medium to obtain a vapour containing cannabinoids and a dispersion with reduced cannabinoids content;
   performing a further extraction on said dispersion with reduced cannabinoids content, which comprises treatment with a polar solvent forming a two-phase system with a first phase of said dispersion and a second phase of said polar solvent, wherein at least part of the cannabinoids from the dispersion with reduced cannabinoids content is extracted into the second phase;
   isolating at least part of the second phase from the first phase and evaporating at least part of said isolated second phase to obtain a cannabinoid containing evaporation residue, and optionally
   dissolving said cannabinoid containing evaporation residue in oil to form a miscella; and
   using said miscella in step a).

7. The process according to claim 2, wherein during said stripping step:
   the temperature of said oil is maintained below 250° C.

8. The process according to claim 2, wherein during said stripping step:
   the pressure is maintained below 20 mbar absolute.

9. The process according to claim 2, wherein said vapour containing said cannabinoids obtained during said stripping step is compressed before being at least partially condensed.

10. The process according to claim 2, wherein said gaseous stripping medium is water vapour.

11. The process according to claim 1, wherein said step of isolating in step b) comprises:
    mixing said dispersion with a polar solvent, and forming a two-phase system with a first phase of said dispersion and a second phase of said polar solvent, wherein at least part of the cannabinoids is extracted into the second phase; isolating at least part of the second phase from the first phase; and wherein the extraction is optionally followed by
    evaporating at least part of said isolated second phase to obtain a cannabinoid containing evaporation residue.

12. The process according to claim 1, wherein said polar solvent is selected from the group consisting of methanol, ethanol, isopropanol, water and mixtures thereof.

13. The process according to claim 1, wherein the dispersion is a solution comprising cannabinoids and other compounds in oil.

14. The process according to claim 1, wherein the dispersion is a suspension containing *Cannabis* plant pieces in oil.

15. A process for obtaining a cannabinoid product, comprising
    the steps of obtaining a cannabinoid extract in accordance with claim 1; and
    adding one or more flavours or aromas to said extract.

16. A process for obtaining a cannabinoid product comprising:
    extracting and separating one or more terpenes from the dispersion obtained by claim 1, and
    adding at least a portion of said one or more terpenes to the cannabinoid extract.

17. The process of claim 16, wherein the dispersion is a solution comprising cannabinoids and other compounds in oil.

18. The process of claim 16, wherein the dispersion is a suspension containing *Cannabis* plant pieces in oil.

19. The process of claim 2, wherein during said stripping step:
the pressure is maintained below 10 mbar absolute.

20. The process of claim 2, wherein during said stripping step:
the pressure is maintained below 5 mbar absolute.

* * * * *

UNITED STATES PATENT AND TRADEMARK OFFICE
CERTIFICATE OF CORRECTION

PATENT NO. : 10,428,040 B2
APPLICATION NO. : 16/125457
DATED : October 1, 2019
INVENTOR(S) : Dijkstra Page 1 of 1

It is certified that error appears in the above-identified patent and that said Letters Patent is hereby corrected as shown below:

In the Claims

Claim 6, Column 16, Line 5, "step b1" should be --step b)--.

Signed and Sealed this
Twenty-fourth Day of September, 2024

Katherine Kelly Vidal
*Director of the United States Patent and Trademark Office*